United States Patent [19]

Priebe et al.

[11] Patent Number: 5,132,290
[45] Date of Patent: Jul. 21, 1992

[54] ESTERS OF 3'-DEAMINODOXORUBICIN AND LIPOSOMAL COMPOSITIONS THEREOF

[75] Inventors: Waldemar Priebe; Roman Perez-Soler, both of Houston, Tex.

[73] Assignee: The Board of Regents, The University of Texas System, Austin, Tex.

[21] Appl. No.: 361,796

[22] Filed: May 30, 1989

Related U.S. Application Data

[63] Continuation of Ser. No. 145,271, Jan. 19, 1988, abandoned.

[51] Int. Cl.$^5$ .................. A61K 31/70; C07H 15/24
[52] U.S. Cl. .................... 514/34; 536/6.4; 424/450
[58] Field of Search .............. 536/6.4; 514/34; 424/450

[56] References Cited

U.S. PATENT DOCUMENTS

| | | | |
|---|---|---|---|
| 3,590,028 | 6/1971 | Arcamone et al. | 536/6.4 |
| 3,803,124 | 4/1974 | Arcamone et al. | 536/6.4 |
| 3,970,641 | 7/1976 | Jolles et al. | 536/6.4 |
| 3,988,315 | 10/1976 | Umezawa et al. | 536/6.4 |
| 3,993,754 | 11/1976 | Rahman et al. | 514/34 |
| 4,031,211 | 6/1977 | Patelli et al. | 514/34 |
| 4,035,566 | 7/1977 | Israel et al. | 536/6.4 |
| 4,067,969 | 1/1978 | Penco et al. | 514/34 |
| 4,166,848 | 9/1979 | Bernardi et al. | 536/6.4 |
| 4,186,183 | 12/1980 | Steck et al. | 424/450 |
| 4,201,773 | 5/1980 | Horton et al. | 536/6.4 |
| 4,229,360 | 10/1980 | Schneider et al. | 264/4.6 |
| 4,235,871 | 11/1980 | Papahadjopoulos et al. | 424/450 |
| 4,241,046 | 12/1980 | Papahadjopoulos et al. | 424/450 |
| 4,247,411 | 1/1981 | Vanlerberghe et al. | 264/4.6 |
| 4,316,983 | 2/1982 | Bollag et al. | 536/17.2 |
| 4,330,534 | 5/1982 | Sakurai et al. | 514/26 |
| 4,351,937 | 9/1982 | Stefanska et al. | 536/6.4 |
| 4,373,094 | 2/1983 | Oki et al. | 536/6.4 |
| 4,419,348 | 12/1983 | Rahman et al. | 514/34 |
| 4,460,577 | 7/1984 | Moro et al. | 424/450 |
| 4,515,736 | 5/1985 | Deamer | 264/4.3 |
| 4,522,803 | 6/1985 | Lenk et al. | 424/1.1 |
| 4,529,561 | 7/1985 | Hunt et al. | 264/4.3 |
| 4,537,882 | 8/1985 | Horton et al. | 514/34 |
| 4,663,167 | 5/1987 | Lopez-Berestein | 514/37 |
| 4,684,629 | 8/1987 | Bargiotti et al. | 514/34 |
| 4,812,312 | 3/1989 | Lopez-Berestein et al. | 424/417 |
| 4,863,739 | 9/1989 | Perez-Soler et al. | 424/450 |

FOREIGN PATENT DOCUMENTS

| | | |
|---|---|---|
| 053827 | 6/1982 | European Pat. Off. |
| 0116222 | 12/1983 | European Pat. Off. |
| 0198765 | 4/1986 | European Pat. Off. |
| 0219922 | 4/1986 | European Pat. Off. |
| WO8500968 | 3/1985 | PCT Int'l Appl. |
| WO86/01102 | 2/1986 | PCT Int'l Appl. |

OTHER PUBLICATIONS

International Search Report.
Perez-Soler et al. (Cancer Research 46:6269).
Ganapathi et al. (Biochem. Pharmacol. 33:698).
Olson et al. (Eur. J. Cancer Clin. Oncol. 18:167).
Sears European patent application No. 0-113-508.
The Merck Index, Entry Nos. 3428 and 2815, 1976.
Horton et al., The Journal of Antibiotics, p. 853, Aug. 1984.
Szoka et al., "Ann. Rev. Biophys. BioEng." (1980) 9:467–508.
Ganapathi et al., "Biochemical Pharmacology", 33:698–700 (1984).
Olsen et al., "Eur. J. Cancer Clin. Oncol.", 18:167–176 (1982).
Horton et al., *Carbohydrate Research*, 136:391–396 (1985).
Danishefsky et al., *J. Org. Chem.*, 47:1597–98 (1982).
Tatsuta et al., *Bulletin of the Chemical Society of Japan* 51:3035–38 (1978).

*Primary Examiner*—Johnnie R. Brown
*Assistant Examiner*—Elli Peselev
*Attorney, Agent, or Firm*—Arnold, White & Durkee

[57] ABSTRACT

Three'-deaminodoxorubicin esters have been found to have excellent encapsulization efficiency in liposomes and to display high antineoplastic activity. The liposomal formulations have also been found to be quite stable.

3 Claims, No Drawings

ESTERS OF 3'-DEAMINODOXORUBICIN AND LIPOSOMAL COMPOSITIONS THEREOF

The present application is a continuation of application Ser. No. 07/145,271 filed Jan. 19, 1988, now abandoned.

FIELD OF THE INVENTION

The present invention relates to derivatives of doxorubicin, liposomal formulations thereof, and methods of using such derivatives and formulations to inhibit neoplastic cell growth.

BACKGROUND OF THE INVENTION

Doxorubicin is known to be an affective anti-neoplastic agent. Some of its derivatives also are known to have such activity. However, undesired side effects like cardiotoxicity and bone marrow toxicity limit its use. Several investigators have shown previously that liposome encapsulation of doxorubicin results in enhanced antitumor activity against liver tumors and decreased cardiotoxicity. However, because doxorubicin is highly hydrophilic, the encapsulation and stability of liposomal doxorubicin are poor, and as a result all known attempts to obtain a satisfactory liposomal doxorubicin formulation have failed.

A compound which has the antitumor activity of doxorubicin but is more amenable to liposome encapsulation would have significant therapeutic advantages. A long standing need exists for such a compound.

SUMMARY OF THE INVENTION

The present invention includes compounds having the general formula

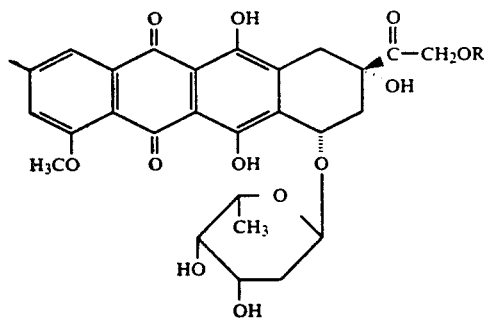

and pharmaceutically acceptable salts thereof. R can be an acyl group having from 1 to 20 carbon atoms.

Compounds in accordance with the present invention can be readily encapsulated in liposomes. The resulting liposomes are highly stable, and in tests conducted so far have demonstrated greater activity in vivo than doxorubicin itself.

The compounds and liposomal formulations of the present invention are useful in methods of inhibiting neoplastic cell growth. Such methods involve administration of an effective amount of the compound or liposome-encapsulated composition, usually with a pharmaceutically acceptable carrier or diluent, to a human being.

DETAILED DESCRIPTION OF A SPECIFIC EMBODIMENT

Compounds in accordance with the present invention have the general formula

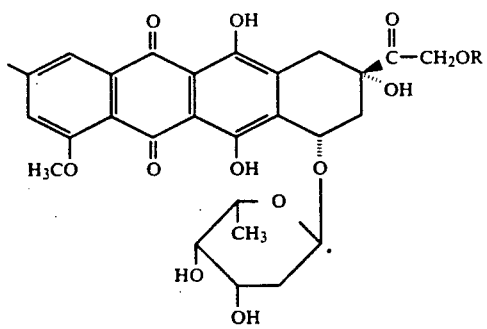

where R can be an acyl group having from 1 to 20 carbon atoms. Pharmaceutically acceptable salts of the above described compounds are also included in the present invention. R is preferably aliphatic. For example, it cam be $-CO(CH_2)_nCH_3$, where n is from 0-18. Long chain acyl groups such as lauroyl, myristoyl, palmitoyl, and stearoyl should be particularly useful. Many other acyl groups should be suitable as well.

The following is an example of how a compound in accordance with the present invention, 7-0-(2,6-dideoxy-α-L-lyxo-hexopyranosyl)-14-0-palmitoyladriamycinone, has been synthesized. Substrate 7-0(2,6-dideoxy-α-L-lyxo-hexopyranosyl)adriamycinone was prepared in five steps by the procedure described by D. Horton, W. Priebe, O. Varela, J. Antibiotics 37 (8), 853–858, (1984).

The synthesis as described in that paper is based on an intermediate, 14-O-tert-Butyldimethylsilyl-7-O-(3,4-di-O-acetyl-2,6-dideoxy -α-L-lyxo-hexopyranosyl) adriamycinone, when can be prepared from one of two precursors, 7-0-(3,4-di-0-acetyl-2,6-dideoxy-α-L-lyxo-hexopyranosyl)adriamycinone or 14-0-tert-Butyldimethylsilyladriamycinone.

14-O-tert-Butyldimethylsilyladriamycinone (Compound A)

To a solution of adriamycinone (0.35g, 0.85 mmol) in DMF (2 ml), imidazole (0.15g, 2.2mmol) and tert-butylchlorodimethylsilane (0.13g, 0.86mmol) were added, and the mixture was stirred at 25° C. After 2 hours, the same quantites as before of imidazole and the silylating reagent were added. The mixture was stirred for 1 hour at room temperature and then diluted with $CH_2Cl_2$ (200 ml), washed with 5% HCl (50 ml) and $H_2O$ (50 ml), and dried over magnesium sulfate containing approximately 0.5 g of sodium carbonate. The mixture was filtered and the filtrate evaporated. The residue crystallized upon addition of absolute EtOH; yield 0.27 g. The mother liquors were evaporated and the residue purified by column chromatography on silica gel (30 g), with 9:1, toluene-acetone as eluant. Fractions containing the product of Rf 0.51 (3:1, toluene-acetone) were pooled and evaporated. The 14-silylated adriamycinone (0.1 g) precipitated from an ethereal solution upon addition of hexane; the overall yield was 0.37 g (82.5%), mp 205° C.

14-O-tert-Butyldimethylsilyl-7-O-(3,4-di-O-acetyl-2,6-dideoxy-α-L-lyxo-hexopyranosyl) adriamycinone (Compound B)

This compound was prepared by two different procedures.

(a) A mixture of compound A (541.2 mg, 1.02 mmol), yellow mercuric oxide (807 mg), mercuric bromide (55 mg) and powdered molecular sieve 4 Å (~2g) in $CH_2Cl_2$ (30 ml) was stirred for 0.5 hour at 25° C., and then a solution of its chloride, prepared from 426 mg (2mmol) of 3,4-di-O-acetyl-L-fucal in $CH_2Cl_2$, was added. The mixture was stirred overnight at 25° C., diluted with 50 ml of $CH_2Cl_2$, and filtered through Celite. The filtrate was washed with 10% aqueous potassium iodide (2×30 ml) and twice with an excess of $H_2O$. The organic layer was dried with magnesium sulfate, filtered, and evaporated under diminished pressure, affording a red oil that crystallized from acetone-ethyl ether-hexane; yield 627 mg (82.5%), mp 132–34° C.

7-O-(3,4-Di-O-acetyl-2,6-dideoxy-α-L-lyxo-hexopyranosyl)adriamycinone (Compound C)

Compound C 0.44 g, 0.7 mmol) was dissolved in dry DMF (2 ml). To this solution were added imidazole (0.12 g, 1.76 mmol) and tert-butylchlorodimethylsilane (0.137 g, 0.91 mmol) and the mixture was stirred for 20 hours at room temperature. TLC monitoring showed some starting material remaining, and so additional silylating reagent (0.06 g, 0.4 mmol) was added. After an additional 2 hours, the starting material had disappeared. The mixture was poured into $H_2O$ (30 ml) and extracted with $CH_2Cl_2$ (100 ml, twice). The extract was washed with 5% HCl (50 ml), $H_2O$ (50 ml) and 10% aqueous sodium hydrogencarbonate, dried over magnesium sulfate, and evaporated. The residue was dissolved in $CH_2Cl_2$ (2 ml) and reprecipitated by addition of hexane; yield 0.44 g (84.6%).

14-O-tert-Butyldimethylsilyl-7-O-(2,6-dideoxy-α-L-lyxo-hexopyranosyl)adriamycinone (Compound D)

Compound B (0.40 g, 0.54 mmol) was dissolved in MeOH (30 ml) and the solution was stirred for 1 hour at 25° C. with 25% sodium methoxide in MeOH (0.31 ml, 1.35mmol). The mixture was made neutral by the addition of dry ice and evaporated to 15 ml under diminished pressure. The solution was diluted with $CH_2Cl_2$ (200 ml), extracted with $H_2O$ (50 ml, twice), drived over magnesium sulfate, and evaporated. The residue was dissolved in a small volume of hot MeOH, and the product precipitated upon cooling; yield 0.31g (88%) of a solid that was sufficiently pure for the next step of the synthesis. Further purification could be achieved by dissolving the solid in the minimal amount of $CH_2Cl_2$ and addition of ether; Rf 0.2 (1:1 toluene-acetone); mp 227° C.

7-O-(2,6-Dideoxy-α-L-lyxo-hexopyranosyl)adriamycinone (Compound E)

Compound D (0.20g, 0.3mmol) was dissolved in a mixture of $CH_2Cl_2$ (10 ml), oxolane (20 ml) and pyridine (0.2 ml), and 1M tetrabutylammonium fluoride (0.45 ml, 0.45 mmol) was added. After 1 hour, the mixture was diluted with 400 ml of $CH_2Cl_2$ and extracted with 50-ml portions of saturated NaCl, 5% HCl, $H_2O$ and 10% sodium hydrogencarbonate. The extract was dried over magnesium sulfate and evaporated. Compound E crystallized from a concentrated solution in $CH_2Cl_2$; yield 86 mg. Dilution of the mother liquors with ether gave an additional 52mg; total yield 83%; mp 175° C.

7-O-(2,6-dideoxy-α-L-lyxo-hexopyranosyl)-14-O-palmitoyladriamycinone (Compound WR-1)

7-O-(2,6-dideoxy-o-L-lyxo-hexopyranosyl)adriamycinone (108.0 mg, 0.195 mmol) prepared as described above was dissolved in dry pyridine (3 ml). Palmitoyl chloride (92 mg, 0.335 mmol) (available from Pfaltz and Bauer Inc.) was added, and the reaction was stirred at room temperature and monitored by TLC (toluene-acetone 1:1). TLC was performed on precoated plastic sheets (0.22 mm) and glass plates (0.25mm) of silica gel 60F-254 (E. Merck, Darmstadt, GFR). Components were detected by spraying the plates with 2 M sulfuric acid, with subsequent heating.

After 90 minutes, another portion of palmitoyl chloride (55 mg, 0.20 mmol) was added. The reaction was stopped after 2 hours by pouring the solution into water, followed by extraction with dichloromethane. The organic layer was subsequently washed with a 10% solution of hydrochloric acid, a saturated solution of sodium bicarbonate, and then twice with water. The solution was then dried over sodium sulfate overnight. Filtration and evaporation under diminished pressure at 50° C. led to formation of red thick oil.

Purification by column chromatography on silica gel 60 (230–400 mesh) (E. Merck, Darmstadt, GFR) (22 g) with 2:1 (50 ml), and then 1:1, toluene-acetone as eluant gave 7-O-(2,6-dideoxy-α-L-lyxo-hexopyranosyl)-14-O-palmitoyladriamycinone as a red solid; yield 59 mg (32.4%). $^1H$ and $^{13}C$ NMR spectra were recorded at 200 MHz and 50 MHz, respectively, with an IBM NR/200AF spectrometer: $^{13}C$ NMR (50 MHz, $CDCl_3$) 206.4 (C-13), 186.9, 186.5 (C-5, 12), 173.2 (C=0-ester), 161.0 (C-4), 156.2, 155.7 (C-6, 11), 135.6, 135.4, 133.9, 133.7 (C-2, 6a, 10a, 12a), 120.8 (C-4a), 119.7 (C-1), 118.4 (C-3), 111.5, 111.3, (C-5a, 11a), 101.1 (C-1'), 77.3 (C-9), 71.0, 69.4, 67.1, 65.7 (x2) * (C-3', 4', 5', 7, 14), 56.6 (OMe), 35.2, 33.9, 33.7, 32.5, 31.9, 29.6 (intensity >x5), 29.4, 29.3, 29.1, 24.9, 24.7, 22.6 (C-8, 10, 2', $CH_2$ palmitoyl chain), 16.7 (C-6'), 14.1 ($CH_3$ -palmitoyl chain).

*Overlapping signals of CH and $CH_2$ groups. Confirmed by refocussed INEPT experiment.

The compound prepared as described above, referred to as WR-1, was encapsulated in multilamellar liposomes by mixing in a chloroform solution dimyristoylphosphatidyl choline, dimyristoylphosphatidyl glycerol, and WR-1 at a weight ratio of 10.5:4.5:1. The chloroform was evaporated in a rotary evaporator and a dried lipid film containing the lipids and WR-1 was obtained. Multilamellar liposomes were formed by adding normal saline (1 ml/mg WR-1) to the dried lipid film and hand-shaking for 1 minute.

Liposomal-WR-1 can also be prepared in a lyophilized powder by dissolving the lipids and WR-1 in t-butanol and freeze-drying. Liposomes are formed upon reconstitution of the powder with normal saline and vortexing for 1 minute.

Liposomes were sized in a Coulter Counter. Vesicle size ranged from 1 to 3μm. Encapsulation of WR-1 in the lipid vesicles was assessed by measuring the amount of drug in the supernatant and the pellet after centrifugation of the liposomal-WR-1 preparation. The drug was measured by UV spectrophotometry at 250 nm. The encapsulation efficiency was greater than 99%. Stability of the lipid vesicles was assessed by measuring the amount of WR-1 released after 14 days at 4° C. The stability was found to be greater than 99%.

The antitumor activity of liposomal-WR-1 was tested against L1210 leukemia and liver metastases of M5076 reticulosarcoma in vivo. BDF1 mice were inoculated intraperitoneally on day 0 with 1 million L1210 cells. Treatment was given as a single injection intraperitoneally on day 1. Liposomal-WR-1 at what is believed to be the optimal dose (60 mg/kg) resulted in a % T/C (mean survival of treated animals/mean survival of control animals x 100) of more than 600 with more than 50% of the treated animals alive on day 60. The mean survival of controls was 8 days. Doxorubicin at the optimal dose of 10 mg/kg resulted in a %T/C of 187 with only 1/6 animals alive on day 60.

C57 BL/G mice were inoculated with $2 \times 10^4$ M5076 cells intravenously on day 0. Treatment was given on days 4, 8, and 12 intravenously. Liposomal WR-1 at a dose of 20 mg/kg on days 4, 8, and 12 resulted in a % T/C of 175, while doxorubicin at the optimal dose of 8 mg/kg on days 4, 8, and 12 resulted in a % T/C of 128.

Liposomal formulations in accordance with the present invention include fatty substances such as phospholipids, optionally cholesterol, and the anthracyclines described above. The formulations preferably include anthracycline and phospholipid in a ratio ranging from about 1 to 10 to about 1 to 30, with a 1 to 15 ratio being most preferred.

In addition to the phospholipids listed in the preceding example for the formulation of the liposome vesicles, one or more of the following could also be used.
Phosphatidylglycerol
Phosphatidylcholine
Sphingomyelin
Phosphatidic acid
Phosphatidylserine
Egg phosphatidylcholine
Dilauryloylphosphatidylcholine
Dimyristoylphosphatidylcholine
Dipalmitoylphosphatidylcholine
Distearoylphosphatidylcholine
1-Myristoyl-2-palmitoyl phosphatidylcholine
1-Palmitoyl-2-myristoyl phosphatidylcholine
1-Palmitoyl-2-stearoyl phosphatidylcholine
1-Stearoyl-2-palmitoyl phosphatidylcholine
Dioleoylphosphatidylcholine
Dilauryloylphosphatidylglycerol
Dimyristoylphosphatidylglycerol
Dipalmitoylphosphatidylglycerol
Distearoylphosphatidylglycerol
Dioleoylphosphatidylglycerol
Dimyristoyl phosphatidic acid
Dimyristoyl phosphatidic acid
Dipalmitoyl phosphatidic acid
Dimyristoyl phosphatidylethanol amine
Dipalmitoyl phosphatidylethanol amine
Dimyristoyl phosphatidylserine
Dipalmitoyl phosphatidylserine
Brain phosphatidylserine
Brain sphingomyelin
Dipalmitoyl sphingomyelin
Distearoyl sphingomyelin The presently preferred liposome formulation comprises dimyristoylphosphatidylglycerol and dimyristoylphosphatidylcholine, preferably in a ratio between about 1 to 10 and about 10 to 1. The most preferred ratio at this time is about 3 to 7.

The liposomes of the present invention may be multilamellar, unilamellar or have an undefined lamellar construction. A pharmaceutical composition comprising liposome-encapsulated compounds in accordance with the present invention and a pharmaceutically acceptable carrier or diluent may be used for the therapy of disease conditions such as cancer.

Methods in accordance with the present invention comprise administering to a host an effective amount of the compounds or compositions described above. The administering step is preferably parenteral and by intravenous, intraarterial, intramuscular, intralymphatic, intraperitoneal, subcutaneous, intrapleural or intrathecal injection or by topical application or oral dosage. Such administration is preferably repeated on a timed schedule, for example twice daily for a period of two weeks. The treatment may be maintained until tumor regression or disappearance has been achieved and may be used in conjunction with other forms of tumor therapy such as surgery or chemotherapy with different agents.

The examples and specific description given in this patent application are intended only to illustrate the present invention, not to provide an exhaustive description of all possible embodiments of the present invention. Those skilled in this field would recognize that modifications could be made to the examples given that would remain within the scope of the invention.

We claim:

1. A compound having the formula

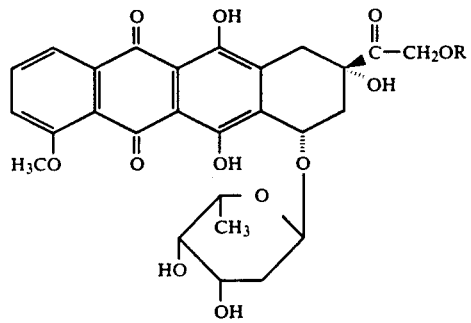

or a pharmaceutically acceptable salt thereof, where R is palmitoyl.

2. A composition comprising a compound having the formula

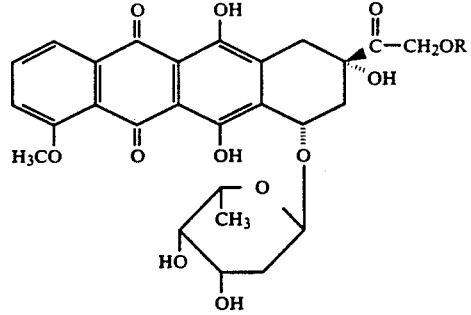

or a pharmaceutically acceptable salt thereof, where R is palmitoyl, the compound being encapsulated in a liposome.

3. The composition of claim 2, where the liposome comprises dimyristoylphosphatidyl choline, dimyristoylphosphatidyl glycerol, and a compound having a formula specified in claim 5, in an approximate weight ratio of 1.5:4.5:1.

UNITED STATES PATENT AND TRADEMARK OFFICE
CERTIFICATE OF CORRECTION

PATENT NO. : 5,132,290
DATED : July 21, 1992
INVENTOR(S) : Priebe, et al

It is certified that error appears in the above-indentified patent and that said Letters Patent is hereby corrected as shown below:

In claim 3, at column 6, line 66, "claim 5" should read -- claim 2--.

Signed and Sealed this

Twenty-fourth Day of August, 1993

Attest:

BRUCE LEHMAN

*Attesting Officer*   *Commissioner of Patents and Trademarks*